United States Patent [19]

Bexendale

[11] Patent Number: 5,378,467
[45] Date of Patent: Jan. 3, 1995

[54] CELL-FREE MAREK'S DISEASE VIRUS VACCINE

[75] Inventor: William Bexendale, Huntingdon, United Kingdom

[73] Assignee: Akzo N.V., Arnhem

[21] Appl. No.: 156,967

[22] Filed: Nov. 23, 1993

Related U.S. Application Data

[63] Continuation of Ser. No. 812,907, Dec. 20, 1991, abandoned.

[30] Foreign Application Priority Data

Dec. 24, 1990 [EP] European Pat. Off. ............ 90314297

[51] Int. Cl.$^6$ .......................... A61K 39/12; C12N 7/08
[52] U.S. Cl. ............................... 424/202.1; 435/235.1; 435/236; 435/237; 424/229.1
[58] Field of Search ............... 424/89; 435/235.1, 237, 435/236

[56] References Cited

U.S. PATENT DOCUMENTS 4,160,024  7/1979  Schat et al.
4,895,718  1/1990  Witter

FOREIGN PATENT DOCUMENTS 8902278  3/1989  WIPO

OTHER PUBLICATIONS

Cho "An Improved Method for Extracting Cell-Free Herpesviruses of Marek's Disease and Turkeys from Infected Cell Cultures Avian Diseases" 22(1) 1978, pp. 170–176.
Witter et al "Biological Diversity Among Serotype 2 Marek's Disease Viruses" Avian Diseases 34, 944–957, Oct.–Dec., 1990.
Cook et al "Preparation of Infectious Cell-Free Herpes-Type Virus Associated with Marek's Disease" J. Vir. 5(2) 1970 pp. 258–261.
Calnek et al "Lyophilization of Cell-Free Marek's Disease Herpesvirus and a Herpesvirus from Turkeys" Applied Micorobology, Nov. 1970 (20(5) pp. 723–726.

*Primary Examiner*—Christine M. Nucker
*Assistant Examiner*—Chris Dubrule
*Attorney, Agent, or Firm*—Mary E. Gormley

[57] ABSTRACT

The present invention is concerned with a vaccine for the protection of poultry against Marek's Disease. The cell free vaccine of the invention facilitates the handling of the vaccine and reduces the chance of physical abuse. The invention also relates to bivalent or polyvalent vaccines comprising in addition other viruses of the Marek's Disease virus group, i.e. HVT.

14 Claims, 2 Drawing Sheets

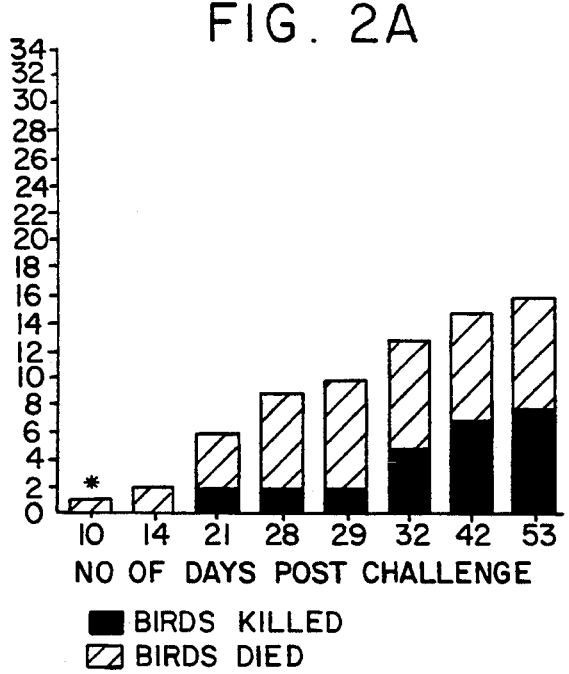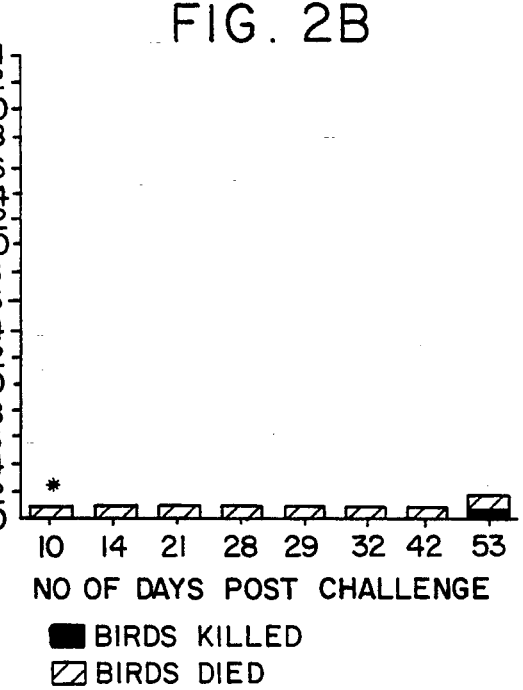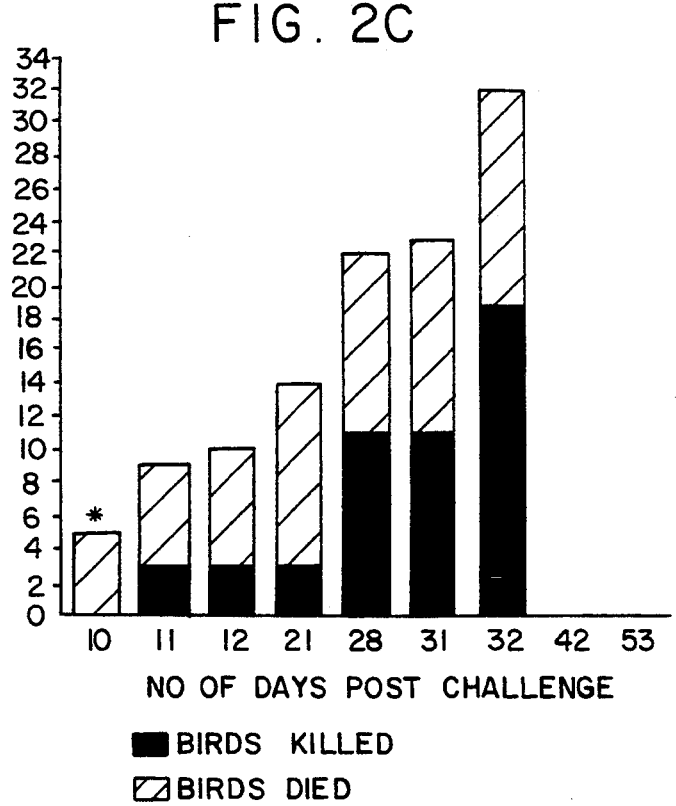

CELL-FREE MAREK'S DISEASE VIRUS VACCINE

This a continuation of application Ser. No. 07/812,907 filed Dec. 20, 1991, now abandoned.

The present invention is concerned with a vaccine for the protection of poultry against Marek's Disease and the method for the preparation of such a vaccine.

BACKGROUND OF THE INVENTION

Marek's Disease (MD) is a malignant, lymphoproliferative disorder of domestic fowl caused by a herpesvirus: Marek's Disease Virus (MDV). MD is ubiquitous, occurring in poultry-producing countries throughout the world. Chickens raised under intensive production systems will inevitably suffer losses from MD. MD affects chickens from about 6 weeks of age, occurring most frequently between ages of 12 and 24 weeks.

Three forms of MD are recognized clinically, classical MD, acute MD and transient paralysis.

Classical MD is characterized by peripheral nerve enlargement caused by lymphoid infiltration and demyelination, and paralysis is the dominant clinical sign. Mortality is variable but normally under 10-15 percent.

In the acute form there are multiple and diffuse lymphomatous tumours in the visceral organs. Mortality from this form of MD is usually higher than from the classical form. An incidence of 10-30 percent is common in unvaccinated flocks and outbreaks involving up to 70% of the flock may be encountered. The pathological lesions in both classical and acute MD are essentially similar, involving the proliferation and infiltration of malignantly transformed T-lymphoblasts into normal tissues, peripheral nerves in the case of the classical form and visceral organs in the case of the acute form.

Furthermore, the MDV has been shown to be responsible for encephalitis of young chickens characterized by sudden paralysis.

Serological classification of MD related viruses yielded three serotypes:

Type I : naturally occurring virulent strains of Marek's disease-virus which are pathogenic and tumorigenic to chickens, and attenuated nonpathogenic strains derived there from Type II: naturally occurring nonpathogenic strains of Marek's disease virus; and Type III: herpesvirus of turkeys ("HVT"), which is nonpathogenic to chickens.

There are several practical Marek's disease vaccine types currently in use. These include vaccines derived from pathogenic serotype 1 strains of MD virus. Serial passage of these strains was found to result in loss of pathogenicity and oncogenicity, but not of immunogenicity. Attenuated viruses derived from strain HPRS-16, the prototype MD vaccine (Churchill, A. E. et al., J. Gen. Virol. 4, 557, 1969) and the CVI-988 strain have already been licensed for commercial use as a live serotype 1 MD vaccine.

Serotype 2 MD viruses are naturally non-oncogenic and thus do not have the potential for causing tumours in vaccinated chickens. Therefore, these viruses do not require any artificial attenuation by serial passaging and since they are in their natural state, can not revert to a virulent form. The HN-1 strain has been shown to be successful in vaccination in addition to the SB-1 strain (U.S. Pat. No. 4,160,024) which has been licensed in the United States since 1983. Hitherto, serotype 1 and serotype 2 vaccines have to be administered as cell-associated preparations (Powell, P. C., World's Poultry Science Journal 42, 205, 1986; Witter, R. L. et al, Avian Diseases 31, 829, 1987; Schat, K. A., Internews 3, 13, 1989). In practise, this means that storage and transportation of said vaccines have to take place in liquid nitrogen at about $-196°$ C.

Errors in vaccine storage and handling result in the decrease of the viability of the MD viruses and cause failure of the vaccination. In particular in countries where liquid nitrogen storage is practically impossible cell-associated MD vaccines are not applicable. Furthermore, the MDV containing particles suspended in a cell-associated vaccine precipitate, require the homogenization of the suspension before administration. Inadequate homogenization may result in an incorrect dose of vaccine and therefore in a failure of the vaccination. Moreover, the strictly cell-associated nature of said vaccines is responsible for the susceptibility of the vaccines to physical abuse. Damage to the infected cells by sub-optimal harvesting and freezing procedures as well as incorrect thawing of the ampules and handling of the vaccine at the hatcheries will cause cell damage and death and subsequent loss of vaccine titres.

Nowadays, a frequently used MD vaccine is derived from HVT. HVT was first isolated from turkeys, is apathogenic in turkeys and in fowls and is antigenically related to serotype 1 and 2 MD viruses. HVT is extensively used as a vaccine against MD, the FC126 strain being most widely used. HVT is commonly used as a cell-associated preparation, but because substantial amounts of cell-free virus can be extracted from infected cells, it may also be used as a lyophilized, cell-free vaccine.

Because of the continued pressure to reduce economic losses from MD to lower levels a need exists to continuously improve the efficacy of MD vaccines, especially now that excessive losses in the poultry industry as a result of the occurrence of very virulent strains of MD virus have been reported both in the US and in Europe. Thusfar, HVT vaccination does not offer adequate protection against such isolates, even at high doses or after extended intervals between vaccination and challenge. The spread of these very virulent field strains of MD virus will be favoured by the relatively inefficient vaccination with HVT alone.

A useful method currently available to control disease caused by infection with the very virulent MD viruses is the use of bivalent or polyvalent vaccines containing mixtures of vaccine viruses belonging to the different serotypes of the MD virus group. It was found that a bivalent vaccine composed of HVT and SB-1 or another serotype 2 MD virus provided better protection than any component virus alone. This phenomenon was termed "protective synergy" designating the mechanism by which the magnitude of the protection afforded by one MD vaccine virus is augmented by the addition of a second vaccine virus (Witter, R. L., Avian Pathology 11, 49, 1982; Witter, R. L. and Lee, L. F., Avian Pathology 13, 75, 1984; Witter, R. L., Avian Diseases 31, 752, 1987; Schat, K. A. et al., Avian Pathology 11, 593, 1982). Disadvantageously, in order to benefit from this synergy the bivalent vaccine has to be a cell-associated preparation as until now a cell-free serotype 2 MD virus vaccine is not available.

MDA (maternal derived antibodies) to all MD viral serotypes are ubiquitous in commercial chicks due to natural exposure of breeders to MD viruses and/or vaccination of breeders with serotype 1, 2 and 3 viruses.

The adverse effect of homologous MDA on vaccination is generally known. MDV antibodies do interfere with (cell-free) HVT vaccine only at a low level. Thus, it is advantageous to be able to vaccinate breeder flocks with HVT-lacking MD virus vaccines in order that their progeny might be better protected with HVT. This so-called alternate generation vaccination has potential merit even when the progeny are vaccinated with HVT-containing bivalent or polyvalent vaccines. However, application of this vaccination strategy requires the availability of a satisfactory HVT-lacking vaccine (Witter, R. L. and Lee, L. F. Avian Pathology 13, 75, 1984). The availability of a vaccine containing a cell-free serotype 2 MD virus, e.g. SB-1, would be very useful in this alternate generation vaccination.

According to the present invention a vaccine is provided for the protection of poultry against MD, characterized in that this vaccine comprises cell-free MD serotype 2 viruses together with a pharmaceutically acceptable carrier.

BRIEF DESCRIPTION OF THE FIGURES

FIG. 2 is a set of histograms showing the incidence of MD after challenge in vaccinated and unvaccinated chicks.

DESCRIPTION OF THE INVENTION

Figure 1A:
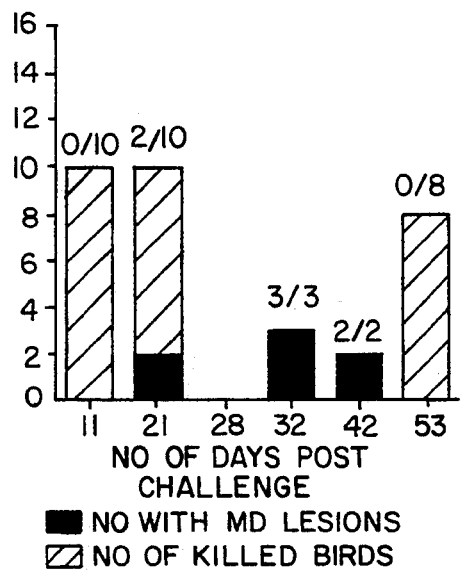
FIG. 1 is a set of histograms that shows the number of birds killed at various times post challenge and the number subsequently found to have MD.
Figure 1B:
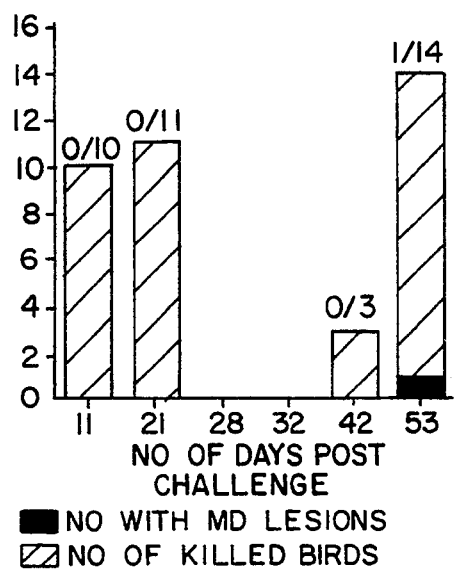
Figure 1C:
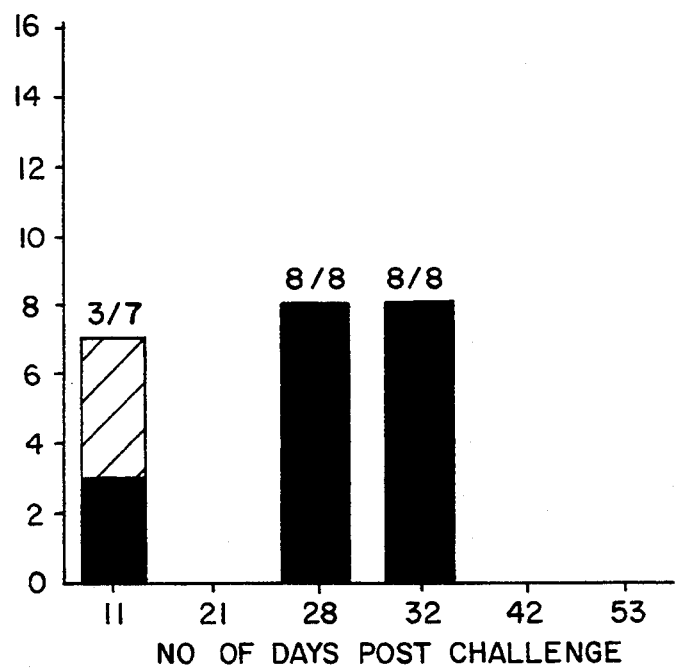

Earlier work with serotype 1 & 2 MD viruses demonstrated that the amount of cell-free virus (measured as primary plaque forming units: pfu) was of inadequate titre to be useful for vaccination purposes (U.S. Pat. No. 4,895,718; Witter, R. L. et al., Avian Diseases 31, 829, 1987; Powell, P. C., World's Poultry Science Journal 42, 205, 1986; Schat, K. A., Internews 3, 13, 1989). In particular, it has been demonstrated therein that the SB-1 virus did not produce significant amount of cell-free virus.

It has now been found that by further passaging serotype 2 MD viruses the amount of cell-free virus was greatly increased and that the cell-free viruses thus obtained still retained their protective properties.

This finding is the more surprising as Witter (Avian Diseases 31, 752, 1987) clearly demonstrated the negative effect of serial passage on the protective efficacy of cell-associated serotype 2 MD viruses.

Furthermore, Witter (ibid, 1987) showed that synergism decreases when the passage number increases: further passaged cell-associated serotype 2 MD viruses did not augment the efficacy of HVT strain FC126 compared to cell-associated serotype 2 MD viruses of low passage number.

Surprisingly, it was found that the magnitude of the protection afforded by cell-free HVT is augmented by the addition of cell-free serotype 2 MD viruses.

The vaccine according to the invention can be obtained by first, serial passaging serotype 2 MD viruses of low passage number, i.e. serotype 2 MD viruses which do not produce sufficient amount of cell-free virus to be useful for vaccine purposes if cultured in an appropriate cell culture, culturing the thus obtained viruses and third processing cell-free viruses obtainable from the culture to a preparation with immunizing properties.

The cell-free vaccine according to the present invention can be derived from any serotype 2 MD virus strain, such as for example the HPRS B-24 strain, the SB-1 strain (Schat et al., U.S. Pat. No. 4,160,024; commercial available from Intervet Inc.), HN-1 strain (Cho, B. R. and Kenzy, S. G. Appl. Microbiol. 24, 299, 1972) or the isolates described by Witter such as the 30/B/1 strain (U.S. Pat. No. 4,895,718, Avian Diseases 31 752, 1987), the SB-1 strain being the most preferred strain.

For the serial passaging of the serotype 2 MD-viruses use can be made of the methods known in the art for this purpose. Briefly, viruses are grown in a suitable cell culture, harvested there from and inoculated to a medium containing a fresh cell culture. The serotype 2 MD viruses are subjected to several serial passages in cell culture until a usable quantity of cell-free virus can be obtained there from, and thereafter processed into a vaccine.

Suitable cell cultures for the serial passaging process are inter alia chick kidney (CK), chicken embryo fibroblast (CEF) and duck embryo fibroblast cultures (DEF).

More in particular, serotype 2 MD viruses can be seeded onto 24 to 48 hour monolayers of CK, CEF or DEF cultures which are then maintained for several days at 37° C. with periodic changes of growth medium. The contents of a suitable growth medium is for example: Eagles basal medium (BME), Tryptose phosphate broth, sodium bicarbonate, Bovine fetal serum and antibiotics. Cells are passaged when 75% or more of the monolayer is cytopathically affected. At the end of the incubation period, the whole mass of cells are washed with phosphate-buffered saline, dispersed with trypsin and resuspended in a small amount of culture medium, and replated and grown on fresh monolayer cell cultures as described above. The number of subsequent passages is dependent of the quantity of cell-free virus obtainable from the culture and of the preservation of the immunogenic and infectious properties of the passaged virus. Cells of the last passage can be washed, trypsinized, centrifuged and dispersed in a small volume of culture medium containing dimethyl sulfoxide (DMSO). This preparation can be slow-frozen to liquid nitrogen temperatures ($-70°$ C.) to be used as seed virus culture.

Typically, cell-free preparations can be obtained according to the method described above which have a titre ranging from $10^4$ to $10^7$ pfu/ml.

The number of passages which are necessary to obtain serotype 2 MD viruses which yield sufficient amounts of cell-free virus is inter alia dependent on the specific serotype 2 MD strain and the desired quantity or titre of cell-free virus.

A typical number of total passages of serotype 2 MD viruses required to prepare a vaccine according to the invention varies between 25 and 40 and is preferably between 28 and 35.

Subsequently, to propagate the serotype 2 MD viruses roller cultures seeded with CEF cells can be inoculated with cell-associated or cell-free virus obtained as described above after 24 hours of incubation. After a further incubation period of several days the supernatant medium is discarded and the cells removed with a trypsin versene mixture whereafter the cells can be deposited by centrifugation and the supernatant is discarded.

In order to prepare the cell-free preparation the deposited cells can be suspended in buffer, for example in phosphate-buffered saline (PBS) or preferably in a medium containing a stabilizer, SPGA (Bovarnik et al., J.

Bacteriology 59, 509, 1950) being the most preferred stabilizer.

Cell disruption may be effectuated by several methods, e.g. sonication or freeze-thaw. The presence of any intact cells can be determined upon examination in a hemocytometer. The sonicated or quick frozen preparation can be filled out in vials and can be freeze-dried if desired in the presence of EDTA. Optionally, before freeze-drying the cellular debris is removed by filtration or centrifugation.

Cell-free serotype 2 MD viruses obtainable from the method described above can be incorporated in vaccines as live viruses or as inactivated viruses.

The vaccines containing live virus can be prepared and marketed in the form of a suspension, or lyophilized.

Lyophilized vaccines can preferably contain one or more stabilizers. Suitable stabilizers are, for example, SPGA (Bovarnik et al., J. Bacteriology 59, 509,950), carbohydrates (such as sorbitol, mannitol, starch, sucrose, dextran or glucose), proteins (such as albumin or casein), or degradation products thereof, protein-containing and buffers (such as alkali methal phosphates). If desired, one or more compounds with adjuvant activity can also be added. Suitable compounds for this purpose are, for example, vitamin-E acetate o/w -emulsion, aluminium hydroxide, phosphate or oxide, mineral oil (such as Bayol F ®, Marcol 52 ® and saponins.

The aim of inactivation of the MD viruses is to eliminate reproduction of the viruses. In general, this can be achieved by chemical or physical means. Chemical inactivation can be effected by treating the viruses with, for example, enzymes, formaldehyde, $\beta$-propiolactone, ethylene-imine or a derivative thereof, an organic solvent (such as a halogenated hydrocarbon) and/or a detergent (such as Tween ®, Triton X ®, sodium desoxy-cholate, sulphobetain or cetyl trimethylammonium salts). If necessary, inactivating substance is neutralized afterwards; material inactivated with formaldehyde can, for example, be neutralized with thiosulphate. Physical inactivation can preferably be carried out by subjecting the viruses to energy-rich radiation, such as UV light, X-radiation or $\gamma$-radiation. If desired, the pH can be brought back to a value of about 7 after treatment.

Usually, an adjuvant (for example such as mentioned above), and, if desired, one or more emulsifiers, such as Tween ® and Span ®, is also added to the inactivated virus material.

The vaccine is administered in an effective dosage of the viral agent, i.e. the amount of immunizing cell-free virus material that will induce immunity in a chicken against challenge by a virulent MD virus. Immunity is defined as the induction of a significant higher level of protection in a population of chickens after vaccination compared to an unvaccinated group.

For live vaccines the dose rate per chick may range from 1 to 6 logs pfu.

Typically, the live vaccine according to the invention is administered in a dose of at least 2.2 logs pfu cell-free virus, preferably in a dose of at least 2.7 logs pfu cell-free virus, more preferably in a dose of at least 3.2 logs pfu.

In the case of a natural route of administration (spray, eye and nose drop) a dose of $10^6$–$10^7$ pfu/chick may be administered.

Inactivated vaccines may contain the antigenic equivalent of 3 to 7 logs pfu per bird dose, preferably between 4 to 6 logs pfu.

Vaccines according to the invention may be administered by spray at high titre, eye drop, nose drop, orally (e.g. drinking water), or by means of intramuscular, subcutaneous or in ovo injection at any age after the chicken obtains immunocompetence. Normally the vaccine is administered to the chick 24–48 hours after hatching.

Another aspect of this invention is the combination of cell-free MD serotype 2 viruses with cell-free HVT as a bivalent vaccine. Surprisingly, it has been found that the cell-free MD serotype 2 viruses are still able to augment the efficacy of HVT, despite the increased stage of passaging.

In particular, cell free serotype 2 MD viruses of the SB-1 strain are used in combination with cell-free HVT. The HVT virus to be incorporated into a vaccine according to the invention may be of any available strain, e.g. FC126 or THV PB1 (commercially available from Intervet Inc.). Optionally, the HVT virus comprises a foreign gene encoding an antigen of a poultry pathogen, inserted into its viral genome, forming a polyvalent vaccine.

The invention also includes combination vaccines comprising in addition to the cell-free serotype 2 MD viral material vaccines derived from other pathogens infectious to poultry. The cell-free serotype 2 MD virus can be administered in combination with a vaccine virus selected from the group consisting of Newcastle Disease virus (NDV), Infectious Bronchitis virus (IBV) and Infectious Bursal Disease virus (IBDV).

EXAMPLE 1

A. Passaging of serotype 2 MD viruses SB-1 and B-24

Cell associated SB-1 or B-24 virus is inoculated onto 24 hour old SPF derived chick embryo cell cultures grown on 6 cm diameter Falcon Petri dishes ($1.5 \times 10^6$ CEF/dish). 0.1 ml of inoculum containing at least 100 pfu is inoculated into the 5 ml of tissue culture medium on the plates and the cell associated virus settles on the monolayer and infects them.

After an incubation period of 5 days at 38.5° C. in a $CO_2$ atmosphere of 5%, the cells are removed from the dishes by 1. pouring off the medium;
2. adding trypsin versene PBS solution to loosen the attachment of the cells to the petri dish;
3. discarding the trypsin/versene PBS mixture before the cells detach from the petri dish;
4. washing the cells off the dishes with growth medium.

The suspension of cell associated virus obtained from step 4 is used as inoculum for the next passage on CEF cells. The viruses were passaged 5 times after receipt as described above. From passage 6 (plus the initial passages) an incubation time of 4 days was adopted.

Results

SB-1

SB-1 virus obtained from Cornell University was already passaged 10 times on receipt (7 tissue culture passages in CEF and CK cells, followed by 2 passages in SPF chicks and a further time passaged on CEF cells).

When heavily infected cells (passage 10 level) from petri dishes were treated in order to obtain cell free virus and resuspended in a volume of 5 ml of SPGA, on assay no live cell free virus was detected at $10^{-2}$ dilution.

When the SB-1 strain was passaged to a total of 21 times after receipt from Cornell University and treated in a similar way a titre of $10^{4.9}$ pfu/ml of live cell free virus was obtained.

SB-1 viruses passaged to a total of 26 times gave rise to a titre of $10^{6.0}$ pfu/ml of cell free virus.

These cell free SB-1 viruses were still infectious to chickens, induced viraemia, spreaded to contact birds and were able to induce a protective immune response.

B-24

When heavily infected cells from the 9th passage of B-24 were treated to obtain cell free virus as described above, the titre was less than $10^2$ pfu/ml.

When heavily infected cells from 35th passage were tested a titre of $10^{4.7}$ pfu/ml was obtained.

B. Preparation of SB-1 cell-free serotype 2 MD vaccine

Two roller cultures (1750 $cm^2$) seeded with $200 \times 10^6$ CEF cells were inoculated into the medium with 1 ml of cell-associated SB-1 seed virus, obtained by the method described above, with a titre of $10^5$ pfu/ml after 24 hours of incubation.

After a further incubation period of 5 days the supernatant medium was discarded and the cells removed with a trypsin versene mixture. The cells were deposited by centrifugation, the supernatant discard and the cells mixed with 20 mls. of SPGA stabilizer and then ultrasonicated for 20 secs.

The sonicated preparation was filled out in 1 ml aliquots in vials and freeze dried.

| | |
|---|---|
| Titre pre freeze drying | $10^{4.8}$ pfu/ml |
| Titre post freeze drying | $10^5$ pfu/ml. |

EXAMPLE 2

Efficacy of cell-free serotype 2 MD vaccine 3 groups of 10 broilers with MDA to serotype 1, 2 and 3 were given different doses of cell-free SB-1 at one day old (i/m).

The doses used were 176 pfu/chick, 460 pfu/chick and 1520 pfu/chick.

The efficacy of the vaccines were tested by the determination of viraemia. Since in earlier experiments it was established that if unvaccinated chicks are placed in contact with chicks vaccinated with SB-1 (high passage) spread is detected in 1 of the 3 contact birds at 2 weeks post-inoculation where the vaccination dose is 200 pfu of cell-associated virus, it was decided not to test for viraemia after 2 weeks. Buffy coats were taken at 1 and 2 weeks post vaccination and tested on CEF cells for SB-1 virus by standard procedures. The cultures were incubated for 1 week before being read. The results reported in Table 1 below indicate that the take rate for chicks which received 176 pfu/chick was at least 56%, whereas all chicks became viraemic after vaccination with 460 pfu/chick or 1520 pfu/chick.

TABLE 1

| Vaccine dose | No. of birds pos./tested Day 14 p.v. |
|---|---|
| 176 pfu | 5/9 |

TABLE 1-continued

| Vaccine dose | No. of birds pos./tested Day 14 p.v. |
|---|---|
| 460 pfu | 10/10 |
| 1520 pfu | 7/7 |

EXAMPLE 3

Comparison of the immunity induced by HVT cell-free and HVT/SB-1 vaccines in MDA positive chickens Viruses—The virus strains used were as follows.

HVT—This is the Intervet PB1 THV strain

SB-1—This strain was further passaged until the virus became rapidly growing and released cell-free virus. Cell-free preparations were made by sonification of infected CEF cells in SPGA stabiliser.

2–3 day old broilers with maternally derived antibody (MDA) to serotype 1, 2 & 3 MD viruses were divided into 3 groups.

| | | |
|---|---|---|
| Group A | 37 chicks | No Vaccine |
| Group B | 42 chicks | Vaccinated with 1000 pfu/chick of HVT vaccine. |
| Group C | 42 chicks | Vaccinated with 1000 pfu/chick of HVT vaccine together with 250 pfu SB-1 virus. |

At 9 days of age all groups were challenged with the virulent virus RBIB

Throughout the experiment, from time to time chicks had to be killed in each group to prevent overcrowding in the isolators.

All chicks that died or were killed were examined for macroscopic and microscopic lesions of Mareks Disease (MD).

Following challenge one chick died at 4 days post challenge (pc) from each of the vaccinated groups, and 5 died between days 5 and 9 from the unvaccinated group. Histological examination revealed lymphoid depletion particularly in the bursa but also in the thymus. These observations together with the timing of the deaths would suggest that they were due to the cytolytic effects of MD.

The histogram in FIG. 1 shows the number of birds killed on each occasion post challenge and the number subsequently found to have Marek's Disease at post mortem or on histological examination.

The histogram in FIG. 2 shows the incidence of MD following challenge in vaccinated and unvaccinated chicks.

A high incidence of MD was observed in the unvaccinated group (FIGS. 1 and 2). Of 7 chicks killed at 11 days pc, 3 had MD tumours. Deaths due to MD started at 11 days pc. At 28 days pc, 8 ill chicks were killed and at 32 days pc all the remaining 8 birds were killed as all but 2 looked severely ill. All 16 chicks had MD tumours in the liver, kidney and other organs. Of a total of 37 birds, 5 appeared to die of "cytolytic MD", 27 had MD tumours or died of MD. The 4 chicks that did not have MD lesions were killed at 11 days pc, giving little time for MD to develop. (One chick died of nonspecific causes.)

In the group that received HVT vaccine macroscopic MD tumours were first seen at 21 days in 2 of 10 chicks killed as well as 2 birds that died at that time. Post mortem examination of 5 sick killed at 32 and 42 days revealed that they all had MD tumours. A total of 7 birds died of MD during the experiment. 8 remaining birds killed 53 days pc had no signs of MD. Of a total of 42 chicks 16 had MD tumours when killed or died of MD. No lesions were found in 10 killed at 11 days pc, 8 killed at 21 days pc and 8 killed at 53 days pc.

The incidence of MD in the dual vaccinated group was very low with only one bird having MD tumours in the liver when killed at 53 days pc. Of a total of 42 chicks 4 died of non-specific causes, one of which may have died of "cytolytic MD". No MD lesions were found in 10 chicks killed at 11 days pc, 11 chicks killed at 21 days pc, 3 birds killed 42 days pc and 13 of the 14 chicks killed at 53 days pc.

The results demonstrate that the cell free dual vaccine SB-1/HVT provided a very high level of protection against a severe challenge of RB1B in broiler chicks with MDA to serotype 2 & 3 viruses.

The HVT vaccine provides significant protection against this severe challenge but approximately 37% of the chicks showed some signs of MD.

It should be noted that because most of the surviving unvaccinated chicks were showing marked clinical signs of MD at about 4 weeks pc, they were all killed by 32 days pc.

On the completion of the experiment at 53 days pc it was observed that the chicks receiving the dual vaccine were heavier than those vaccinated with HVT alone. This is surprising as none of the 8 HVT vaccinated chicks had obviously significant MD lesions when killed.

EXAMPLE 4

Comparison of the immunity induced by cell-free SB-1 virus and HVT/SB-1 vaccines in MDA free chickens 20 day old SPF chicks were inoculated subcutaneously with 200 pfu of the freeze dried cell free SB-1 virus reconstituted in SPGA 0.1 ml/chick. A second group of chicks received 200 pfu of SB-1 vaccine together with 1000 pfu of HVT vaccine virus.

After 1 week these chicks together with 20 unvaccinated chicks of the same origin and age were challenged by i/m inoculation with the virulent strain of RB1B. Over a 6 week period the number of chicks per group that died of Marek's Disease was determined.

TABLE 2

| Vaccine | No. of birds died/tested |
|---------|--------------------------|
| Control | 20/20 |
| SB-1 | 6/20 |
| HVT/SB-1 | 0/20 |

I claim:
1. A vaccine for the protection of poultry against Marek's Disease, comprising cell-free Marek's Disease serotype 2 virus, and a pharmaceutically acceptable carrier.
2. A vaccine according to claim 1, wherein the virus is a cell-free SB-1 virus.
3. A vaccine according to claim 1, wherein the dosage of the cell-free Marek's Disease serotype 2 virus is at least 2.2 log pfu/chick.
4. A vaccine according to claim 3, wherein said dosage is at least 2.7 log pfu/chick.
5. A vaccine according to claim 4, wherein said dosage is at least 3.2 log pfu/chick.
6. A vaccine according to claim 1, additionally comprising cell-free HVT.
7. A vaccine according to claim 1, wherein said vaccine is lyophilized.
8. A method for the preparation of a vaccine that protects poultry against Marek's Disease comprising:
   a) growing a serotype 2 Marek's Disease virus in a cell culture from which sufficient quantities of cell-free virus necessary to prepare an effective immunizing dosage can be obtained,
   b) disrupting the cells, and
   c) collecting the cell-free viruses, and mixing them with cell-free HVT,
such as to prepare an effective immunizing dosage of said vaccine.
9. A method according to claim 8, wherein the titre of cell-free virus after step b is at least 4 logs pfu/ml.
10. A method of controlling Marek's Disease in poultry comprising administering an immunologically effective amount of the vaccine according to claim 1 to poultry.
11. A method according to claim 8, wherein additionally the collected cell-free viruses are clarified by centrifugation or filtration.
12. A method according to claim 8, wherein additionally the collected cell-free viruses are freeze-dried.
13. A method according to claim 8, wherein additionally a buffer is added to the cell-free viruses.
14. A method according to claim 8, wherein additionally a stabilizing agent is added to the cell-free viruses.

* * * * *

UNITED STATES PATENT AND TRADEMARK OFFICE
CERTIFICATE OF CORRECTION

PATENT NO. : 5,378,467
DATED      : January 3, 1995
INVENTOR(S): William M. Baxendale It is certified that error appears in the above-indentified patent and that said Letters Patent is hereby corrected as shown below:

Title page, item [19] and [75], inventors: should read--Baxendale

Signed and Sealed this

Ninth Day of May, 1995

Attest:

BRUCE LEHMAN

Attesting Officer        Commissioner of Patents and Trademarks